(12) United States Patent
Cunningham et al.

(10) Patent No.: US 11,903,575 B2
(45) Date of Patent: *Feb. 20, 2024

(54) ANCHOR DELIVERY SYSTEMS

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Matthew D. Cunningham, Lakeville, MA (US); Rick Fu, Randolph, MA (US); Allison Marie Stauffer, Brighton, MA (US); Geoffrey Karasic, Milton, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 50 days.

This patent is subject to a terminal disclaimer.

(21) Appl. No.: 17/898,527

(22) Filed: Aug. 30, 2022

(65) Prior Publication Data
US 2022/0409198 A1 Dec. 29, 2022

Related U.S. Application Data

(62) Division of application No. 15/930,593, filed on May 13, 2020, now Pat. No. 11,457,911.

(60) Provisional application No. 62/846,788, filed on May 13, 2019.

(51) Int. Cl.
*A61B 17/04* (2006.01)

(52) U.S. Cl.
CPC .. *A61B 17/0401* (2013.01); *A61B 2017/0409* (2013.01); *A61B 2017/0448* (2013.01)

(58) Field of Classification Search
CPC ........ A61B 17/0401; A61B 2017/0409; A61B 2017/0448; A61B 2017/0417; A61B 2017/0464; A61B 2017/06052
See application file for complete search history.

(56) References Cited

U.S. PATENT DOCUMENTS

2018/0116654 A1* 5/2018 Santangelo ........ A61B 17/0469

* cited by examiner

*Primary Examiner* — Tan-Uyen T Ho
*Assistant Examiner* — David P Stein
(74) *Attorney, Agent, or Firm* — Burns & Levinson, LLP; Joseph M. Maraia; Marlo Schepper Grolnic

(57) ABSTRACT

Anchor delivery systems include anchors having a generally cylindrical body with a rail on top for positioning within a delivery device slot. The rail incorporates a side-bulge as a retaining feature which axially extends along a majority of the length of the rail. The bulge interferes with a corresponding hourglass cutout in the delivery device slot to prevent the anchor from stripping out of the delivery device when the delivery device is retracted through tissue. The anchors are symmetrical along a length and width to facilitate loading within the delivery device. The distal portion of the delivery device includes a series of distally-extending barbs that intentionally change the penetration force required to push the device tip through tissue.

15 Claims, 8 Drawing Sheets

ANCHOR DELIVERY SYSTEMS

CROSS-REFERENCE TO RELATED APPLICATIONS

This application is a divisional of co-pending U.S. application Ser. No. 15/930,593, filed May 13, 2020, entitled ANCHOR DELIVERY SYSTEMS, which in turn claims priority to and benefit of U.S. Provisional Application No. 62/846,788, filed May 13, 2019, the entire contents of which are incorporated by reference herein for all purposes.

FIELD

The present disclosure relates generally to surgical anchor delivery systems for repairing soft tissue and, more particularly, to surgical needles and anchors for closing a wound or tear in fibrous tissue.

BACKGROUND

Areas in the body where tissue can be surgically reattached to bone or repaired when a tear forms in the tissue include, but are not limited to, the biceps tendon, the lateral collateral ligament in the knee, the medial collateral ligament in the knee, the meniscus in the knee, and the popliteal ligament in the leg. Fibrous tissue wounds, such as muscle, ligament, and meniscal tears, can be repaired arthroscopically using sutures. Traditionally, to close a fibrous tissue wound, a surgeon would insert two needles into the tissue loaded with sutures attached to an anchor, thread the sutures across the wound, and then tie knots to fix the free ends of the sutures within the tissue.

To simplify wound closure and to improve fixation, various types of anchors, as well as delivery devices for delivering the anchors, have been developed. Some types of delivery devices use two separate actuation members that deploy the anchors in a sequential manner, or a single actuation member that deploys the first anchor then retracts to deploy the second anchor from the delivery device. However, due to their small size, the anchors can sometimes be inadvertently stripped out of the delivery device when the delivery device is retracted through tissue, compromising device function. Typical anchors are also asymmetrical, which can lead to problems when the anchor is mistakenly loaded backward into the delivery device. Furthermore, most anchor delivery devices include a stop feature (usually a tube) to contact the proximal side of the penetrated tissue. Often, a user adjusts the stop feature such that the resulting exposure of the device tip on the distal side of the tissue far exceeds the tissue thickness to ensure that the device tip penetrates the entire tissue thickness. However, allowing for excessive penetration beyond the distal side of tissue could result in damage to surrounding tissue, nerves, arteries, and other structures.

SUMMARY

Described herein are anchor delivery systems in which the anchors include a generally cylindrical body with a rail on top for positioning within a delivery device slot. The rail incorporates a side-bulge as a retaining feature which axially extends along a majority of the length of the rail. The bulge interferes with a corresponding hourglass cutout in the delivery device slot to prevent the anchor from stripping out of the delivery device when the delivery device is retracted through tissue. The anchors are symmetrical along a length and width, meaning that they can be loaded forward or backward into the delivery device without compromising device function. The distal portion of the delivery device also includes a series of distally-extending barbs that intentionally change the penetration force required to push the device tip through tissue. Thus, the anchor delivery systems of this disclosure advantageously provide a means to sense adequate penetration of the device tip through the repair site tissue, while also preventing the anchor being misloaded and/or from inadvertently stripping off of the delivery device. Furthermore, the symmetrical shape of the anchor provides the ability to use the same type of anchor in the anchor/suture construct loaded within the delivery device.

Examples of the anchor delivery systems of this disclosure may include one or more of the following, in any suitable combination.

In examples, an anchor delivery system of this disclosure includes an elongated needle defining an axial bore extending between proximal and distal ends of the needle. The distal end of the needle defines a tissue-penetrating tip and includes one or more distally-extending barbs. The barbs are configured to provide tactile feedback to a user of a tissue penetration force of the needle.

In further examples, the one or more distally-extending barbs is a plurality of barbs, and an outer diameter of each of the plurality of barbs decreases towards the distal end of the needle. In examples, the one or more distally-extending barbs are defined by a sidewall of the distal end of the needle. In examples, the distal end of the needle includes a slot extending from an outer surface of the needle to the axial bore and to the distal end of the needle. In examples, the needle comprises a retention region defined by opposing edges of the slot curving inward towards one another. In examples, the system also includes a suture/anchor construct including first and second anchors having a rail extending from a top surface of a cylindrical body. The suture/anchor construct is disposed within the axial bore of the needle. In examples, each of the first and second anchors are symmetrical along a length and width of the anchor. In examples, a first end and a second end of the rail are sloped toward the cylindrical body. In examples, the first and second anchors are the same.

In examples, an anchor of this disclosure includes a generally cylindrical body having a top surface and a bottom surface. Each of the top and bottom surfaces extend along a longitudinal axis between proximal and distal ends of the body. The anchor also includes a rail extending from the top surface of the body. The rail includes at least one projection extending along a majority of a length of a side of the rail. The at least one projection provides a retaining function when engaged with a mating surface of a delivery device.

In further examples, the anchor is symmetrical along a length and width of the anchor. In examples, the anchor includes a suture pathway having two internal parallel segments each beginning at one end of a respective suture hole in the rail and connected by a third segment. Each segment is configured to slidably accommodate a suture. In examples, the third segment is formed in part by a recess in the bottom surface of the anchor. In examples, a first end and a second end of the rail are sloped toward the cylindrical body. In examples, the anchor is configured for slidable insertion into a bore of a needle having a slot such that the rail extends through the slot of the needle.

In examples, a suture/anchor construct of this disclosure includes a first anchor and a second anchor, and a knotted suture coupling the first and second anchors. In examples, each of the first and second anchors includes a generally cylindrical body having a top surface and a bottom surface. Each of the top and bottom surfaces extend along a longitudinal axis between proximal and distal ends of the body. The first and second anchors further include a rail extending from the top surface of the body. The rail has at least one projection extending along a majority of a length of a side of the rail. The projection provides a retaining function when engaged with a mating surface of a delivery device. In further examples, each of the first and second anchors are symmetrical along a length and width of the anchor. In examples, a first end and a second end of the rail are sloped toward the cylindrical body. In examples, the first and second anchors are the same.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1:
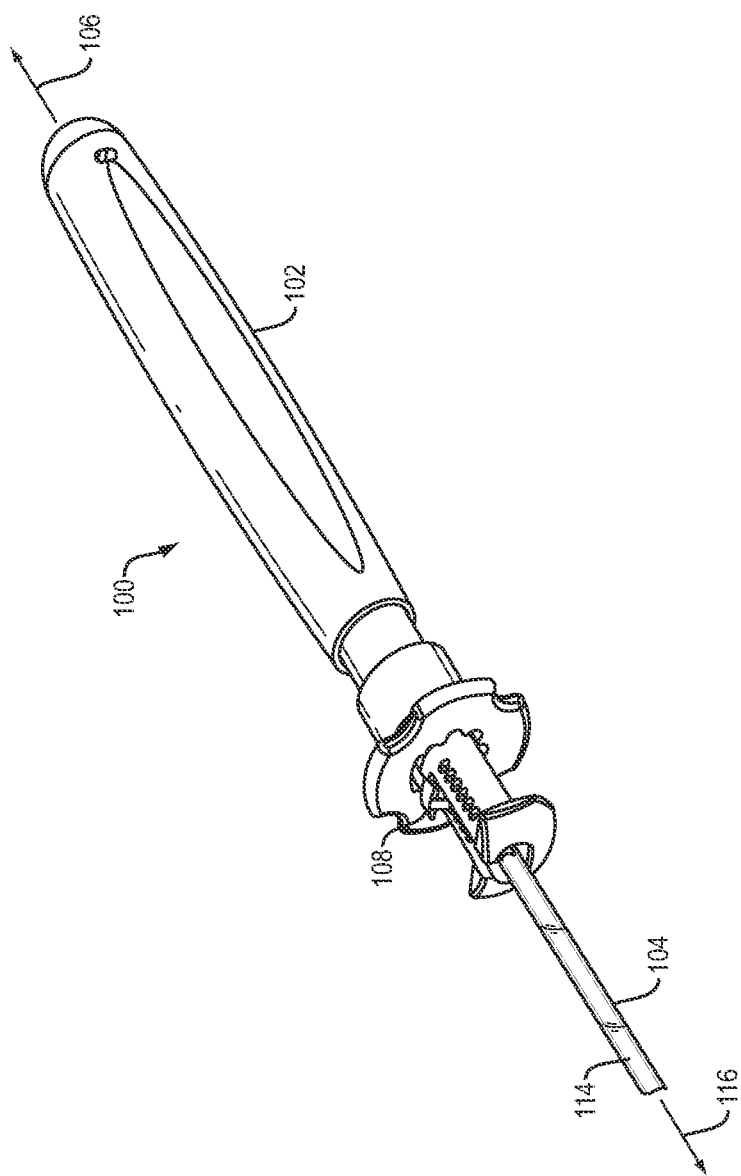
FIGS. 1, 2A and 2B illustrate prior art anchor delivery systems.

In the description that follows, like components have been given the same reference numerals, regardless of whether they are shown in different examples. To illustrate example (s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "top," "bottom," and the like is intended only to help in the clear description of the present disclosure and are not intended to limit the structure, positioning and/or operation of the disclosure in any manner.

For a better understanding of the present disclosure, FIG. 1 shows an example of an anchor delivery system 100 for use in, for example, meniscal repair procedures. The system 100 generally includes a handle 102 and a needle 104 coupled to the handle 102 and extending along a longitudinal axis 106. In examples, the handle 102 is comprised of plastic and needle 104 is comprised of a biocompatible metal, such as stainless steel or titanium. The handle 102 may include an adjustable depth stop 108 for limiting the depth that the needle 104 may be inserted into a tissue site. The needle 104 may extend from the handle 102 and have an inner surface 114 defining an axial bore 116 extending the length of the needle 104.

Figure 2A:
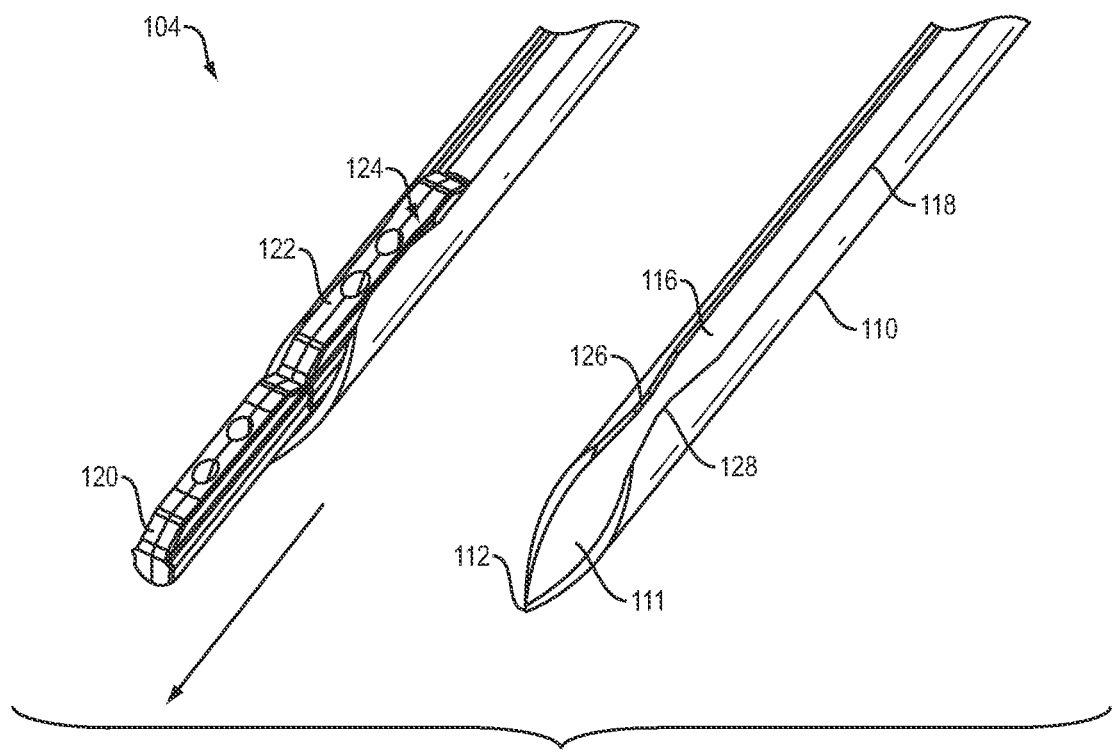
Figure 2B:
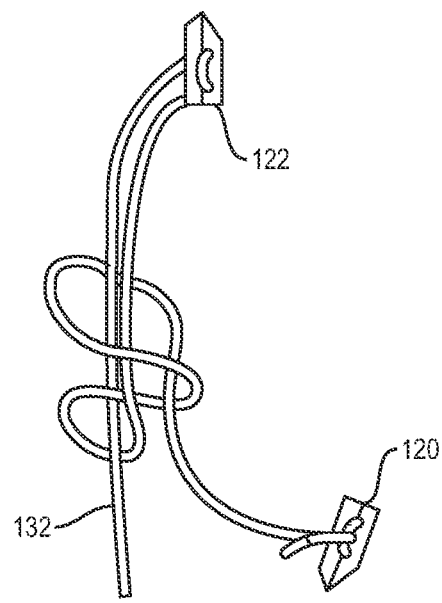

As shown in FIG. 2A, the needle 104 may be configured with a slot 118 extending from an outer surface 110 to the axial bore 116 and to an open distal end 111, which may be beveled to form a pointed, tissue piercing tip 112. The distal end 111 of the needle 104 is configured for at least partially housing a distal anchor 120 and a proximal anchor 122 within the axial bore 116. The proximal anchor 122 and the distal anchor 120 are individually and sequentially deployable from distal end 111 of the needle 104 (for example, with a pusher member), and are connected by a length of knotted suture 132, as shown in FIG. 2B. The slot 118 may include an "hourglass" retention region 124 in which opposing edges 126, 128 of the slot 118 may curve inward towards one another, narrowing the distance between the edges 126, 128 by an amount sufficient to provide a force resisting distal motion of proximal anchor 122 after the distal anchor 120 has been deployed, as further described below. Deploying the distal anchor 120 moves proximal anchor 122 into the retention region 124, as shown. Further non-limiting examples of anchor delivery systems 100 are described in U.S. Publication No. 2018/0116654 to Smith & Nephew, Inc. (Memphis, TN), the contents of which are incorporated by reference herein in their entirety.

Figure 3:
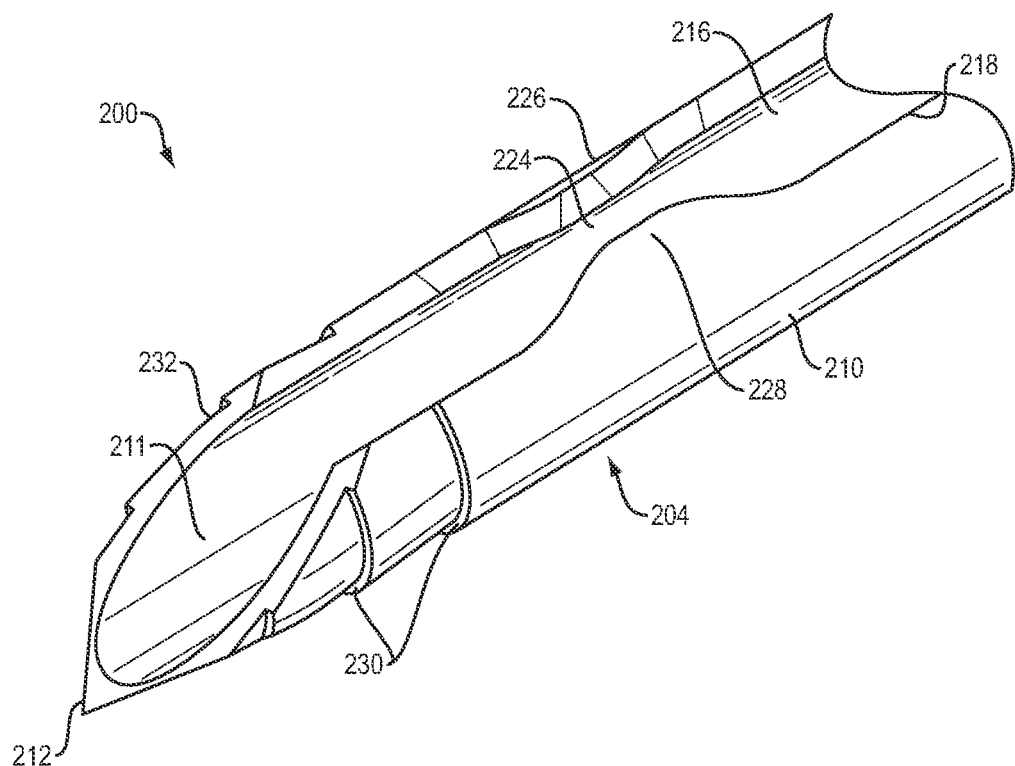
FIG. 3 is a perspective view of a distal end of a needle of an anchor delivery system of this disclosure.

Turning now to FIG. 3, an example of a needle 204 of an anchor delivery system 200 of this disclosure is shown in a perspective view. The anchor delivery system 200 is substantially similar to the anchor delivery system 100, except as described below. In the example of FIG. 3, the needle 204 may be configured with a slot 218 extending from an outer surface 210 of the needle 204 to the axial bore 216 and to an open distal end 211, which may be beveled to form a pointed, tissue piercing tip 212. The slot 218 may include an "hourglass" retention region 224 in which opposing edges 226, 228 of the slot 218 may curve inward towards one another. The distal end 211 of the needle 204 also includes a tactile feature comprising one or more distally-extending barbs 230 defined by a sidewall 232 of the distal end 211 of the needle 204. In examples, an outer diameter of each of the barbs 230 decreases toward to the distal end 211 of the needle 204, such that a thickness of the sidewall 232 also decreases towards to the distal end 211 of the needle 204.

Figure 4:
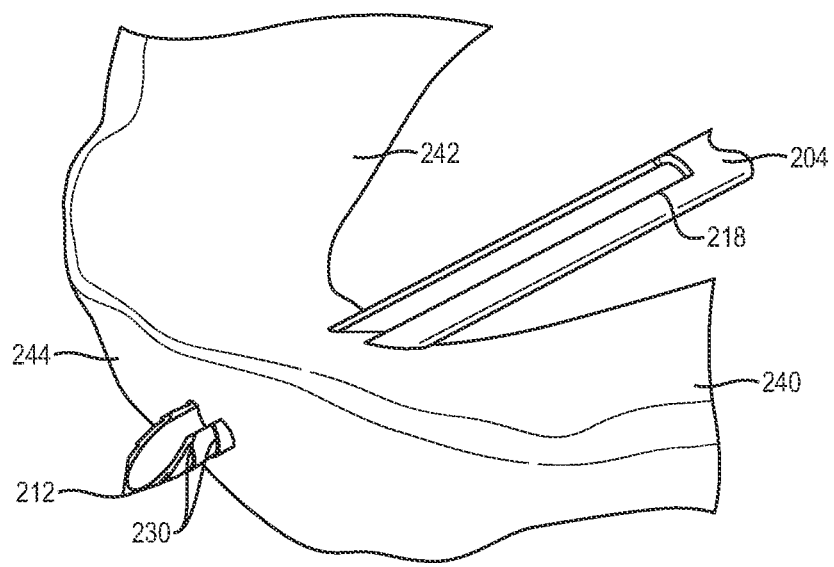
FIG. 4 illustrates a use of the anchor delivery system of FIG. 3 in a tissue repair.

As shown in FIG. 4, the barbs 230 are configured to provide tactile feedback to a user of a tissue penetration force of the needle 204 as the needle 204 is inserted through tissue 240. For example, the user typically holds the delivery system 200 by the handle to position the tip 212 relative to the tissue 240 and applies a sufficient force to penetrate the tissue 240. The tip 212 of the needle 204 initiates penetration on the proximal side 242 of the tissue 240. The penetration force changes once the barbs 230 exit the distal side 244 of the tissue 240. Thus, the barbs 230 can be used to temporarily increase the puncture force of the needle 204 until the barbs 230 have penetrated the tissue 240, or to reduce the puncture force of the needle 204 until the barbs 230 penetrate the tissue 240 and exit the distal side 244 of the tissue 240. Advantageously, use of the tactile feature means that the user does not have to pre-measure the thickness of the tissue 240 and set the appropriate exposure of the needle 204 on the distal side 244 of the tissue 240 with a depth stop tube before penetrating the tissue 240.

Figure 5:
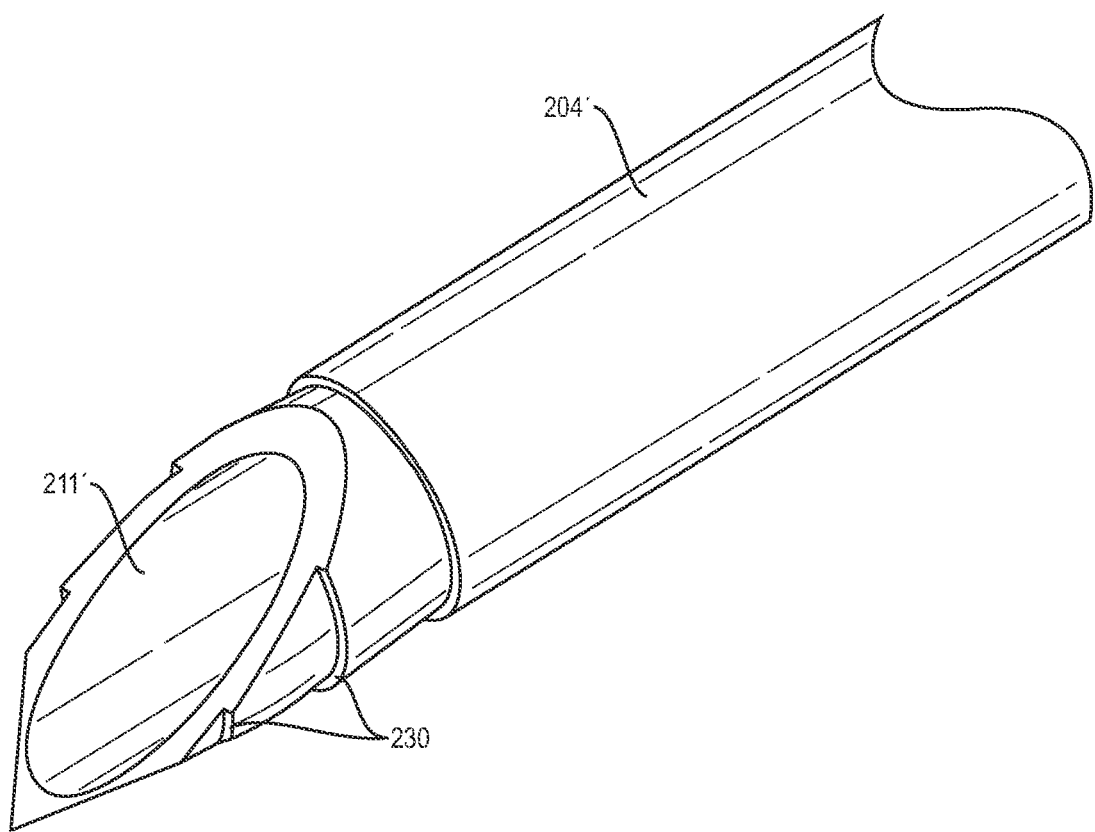
FIG. 5 is an alternative example of the anchor delivery system of FIG. 3.

Notably, while the barbs 230 are shown in FIGS. 3 and 4 on the distal end 211 of the needle 204 having a slot 218, the barbs 230 could also be used on the distal end 211' of a non-slotted needle 204' as shown in FIG. 5. In other examples, not shown, instead of a plurality of barbs 230, the tactile feature on the distal end 211 of the needle 204 could comprise a laser abraded surface treatment, a knurled surface, or a coating that increases or decreases the penetration force of the needle 204. In yet further examples, not shown, the tactile feature could include one or more dimples formed on the inside surface of the depth stop tube through which the needle 204 passes. It is contemplated by this disclosure that material could also be added to the inner surface of the depth stop tube by additive manufacturing means.

Figure 6A:
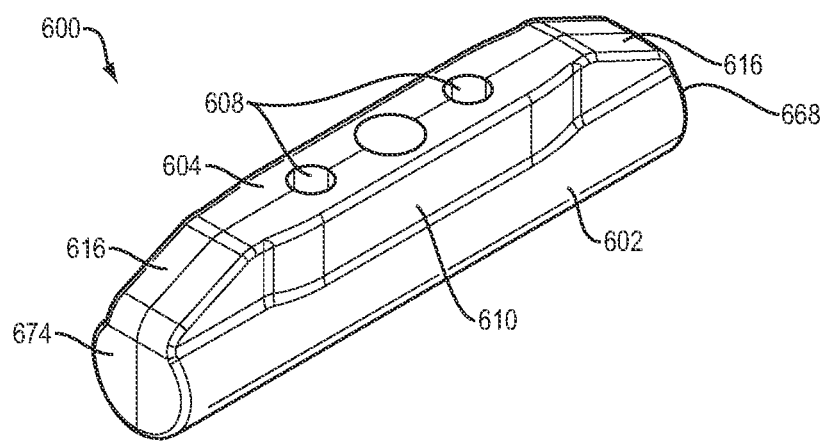
FIGS. 6A-C are perspective, bottom, and cross-sectional views, respectively, of an example of an anchor of the anchor delivery system of this disclosure.
Figure 6B:
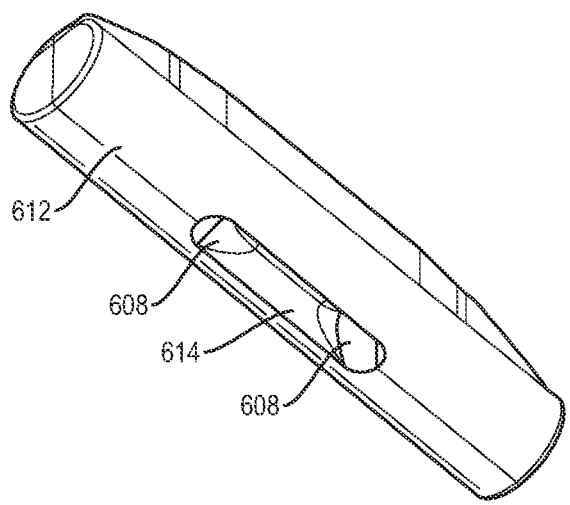
Figure 6C:
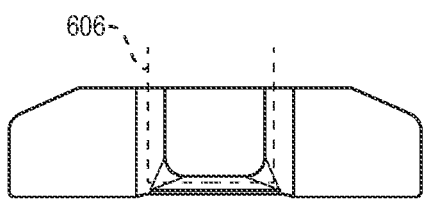

Turning now to FIGS. 6A-C, side, bottom, and cross-sectional views, respectively, of an anchor 600 of this disclosure are shown. The anchor 600 can be used in a delivery system, such as the delivery system 200 of FIGS. 3 and 4. In examples, the anchor 600 is made from rigid, biocompatible materials, such as polyethylene, an acetal, or polypropylene. Alternatively, the anchor 600 can be made from metal, resiliently deformable materials, or from bioabsorbable materials. The anchor 600 is preferably a unitary, injection molded piece, but can also be manufactured by other methods. In examples, the anchor 600 has an elongate, generally cylindrical body 602 being dimensioned to conform to the cross-sectional area of the axial bore 216 of the needle 204 so that it can be received in a close sliding fit within the needle 204. While a cylindrical body is shown in FIGS. 6A-C, it is contemplated by this disclosure that other shapes of the body 602, such as a slab, may also be used. The anchor 600 may also have a rail 604 (e.g., a protrusion, rib, fin, etc.) extending from a top surface of the body 602 from the distal end 674 to the proximal end 668 of the body 602. Each end of the rail 604 may include a beveled end 616 which is sloped toward the body 602. The slope of the beveled end 616 is intended to match the angle of the distal end 211 of the needle 204 to facilitate puncturing tissue. In examples, the anchor 600 is configured with additional material on the sides of the rail 604, the purpose of which will be described in more detail below. The additional material may be in the form of a projection 610 extending along a majority of the length of the sides of the rail 604 between the beveled ends 616. Advantageously, the anchor 600 is symmetrical along both a length and width of the anchor 600, which eliminates the ability to accidentally load the anchor 600 backwards into the axial bore 216. The symmetrical configuration of the anchor 600 also means that the same type of anchor 600 can be used as both the proximal and the distal anchor in a suture/anchor construct, such as the suture/anchor construct shown in FIG. 2B.

Figure 7A:
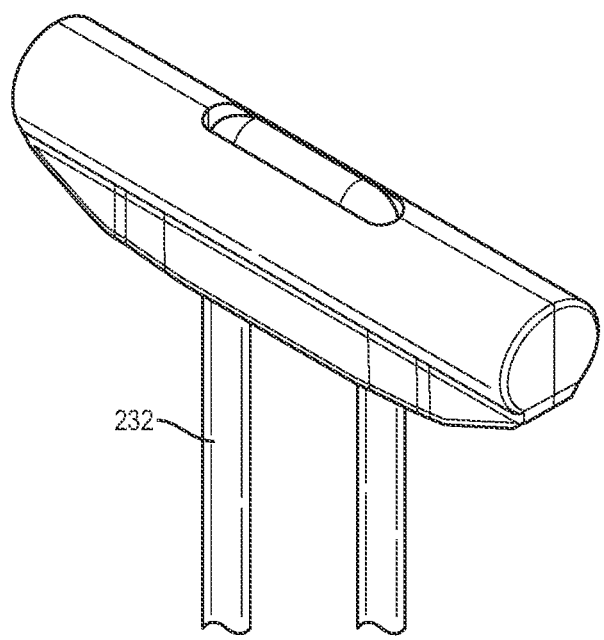
FIGS. 7A and 7B illustrate a suture pathway for the anchors of FIGS. 6A-C.
Figure 7B:
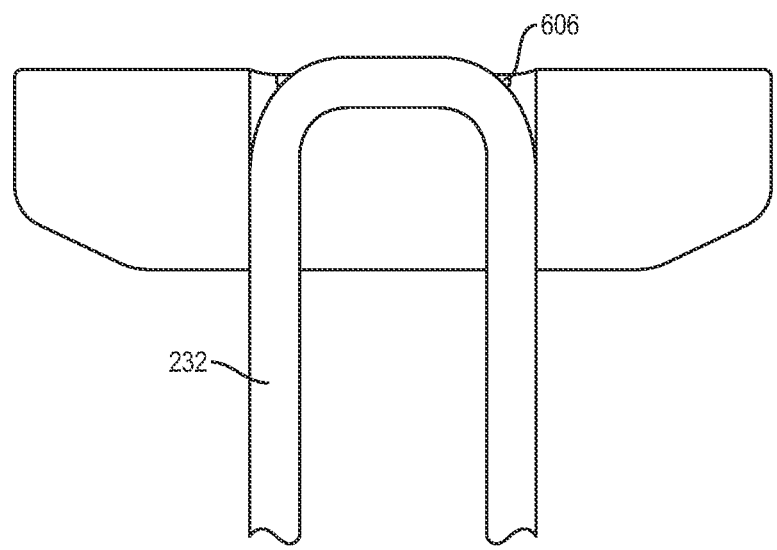

Still referring to FIGS. 6A-C, each anchor 600 may be configured with an internal suture pathway 606 through which a suture may be threaded. The suture pathway 606 begins and ends at the top of suture holes 608. This configuration advantageously results in positioning the necessarily exposed portion of the suture (i.e., the portion connecting anchors 600) outside of the axial bore 216, so that the exposed portion of suture does not interfere with the deployment of the anchor 600, and the risk of the suture being inadvertently cut is minimized. As shown in FIG. 6B, the "bottom" side 612 of anchor 600 may be configured with a length-wise recess 614 forming the bottom of a "U" shaped example of the suture pathway 606, and providing a tight enough fit to secure a portion of suture. Notably, while the suture holes 608 are shown in FIGS. 6A-C as positioned parallel to each other and extending vertically through the anchor 600, the orientation of the suture holes 608 can vary. For example, the suture holes 608 may be positioned horizontally, and they may be angled toward one another. FIGS. 7A and 7B illustrate a suture 232 threaded through the suture pathway 606 in a perspective view (FIG. 7A) and a cross-sectional view (FIG. 7B).

Figure 8:
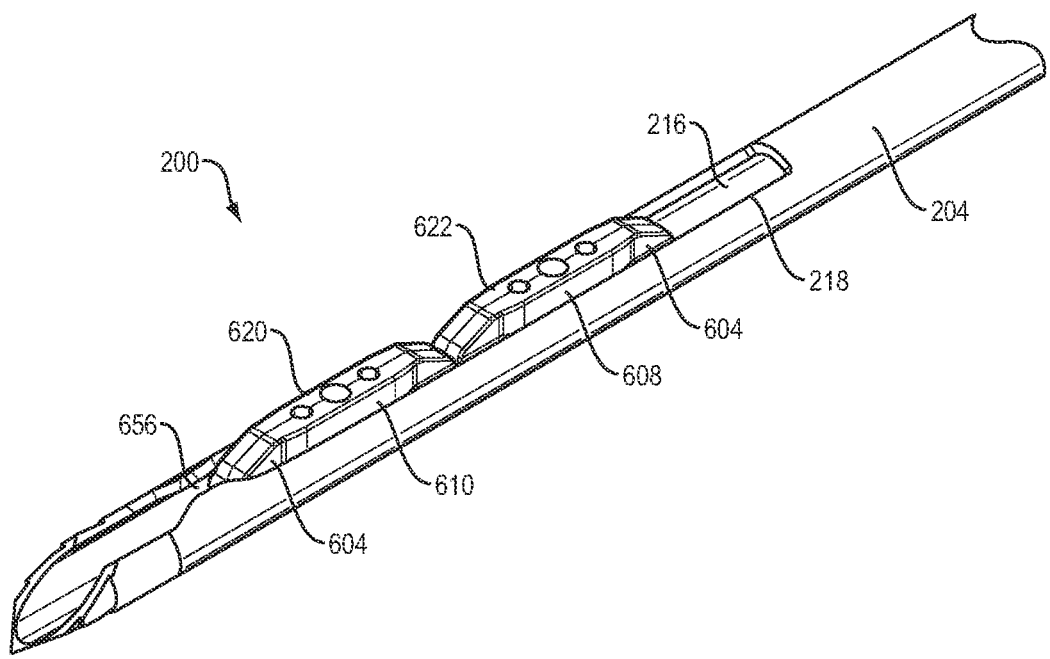
FIG. 8 illustrates a use of the anchors of FIGS. 6A-C in a tissue repair device.

Turning now to FIG. 8, during use of the anchor delivery system 200, the rails 604 of the proximal anchor 622 and the distal anchor 620 are intended to extend out of the axial bore 216 of the needle 204, whereby the rails 604 are slidingly received by the slot 218. The sliding accommodation of each rail 604 by the slot 218 operates so as to maintain radial alignment of the proximal and distal anchors 622, 620 within the needle 204. Furthermore, when the projections 610 are located within the slot 218, the retention region 656 has a width that is narrower than the width of the proximal and distal anchors 622, 620 at the projections 610. It is at the position of the retention region 656 where additional compression force is desired to prevent the proximal anchor 622 from being expelled from the needle 204 while the needle 204 is being removed from the tissue. Thus, the additional compression force at the retention region 656 between the needle 204 and the proximal anchor 622 prevents unintended distal movement of the proximal anchor 622.

Figure 9:
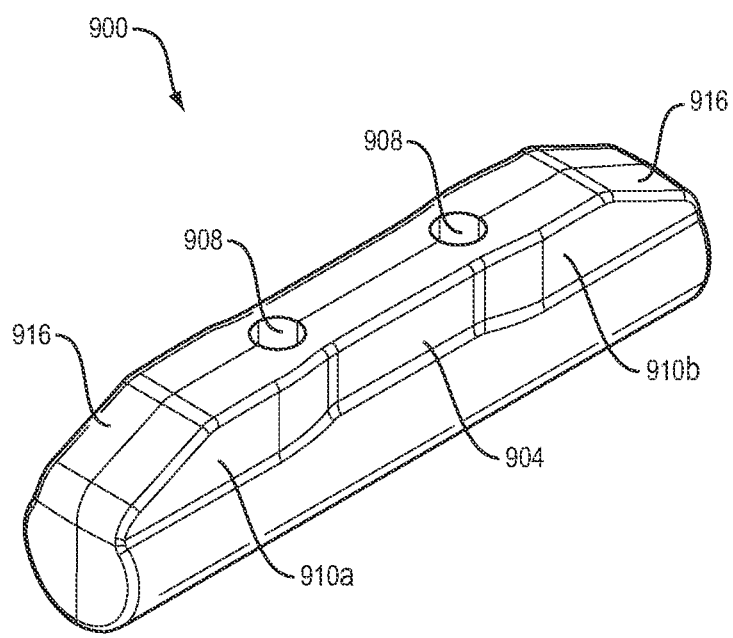
FIGS. 9-11 are alternative examples of the anchors of FIGS. 6A-C.
Figure 10:
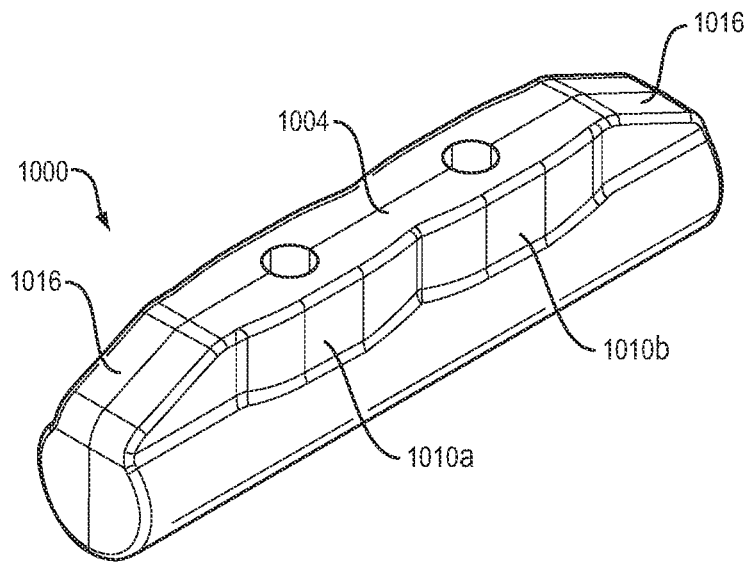
Figure 11:
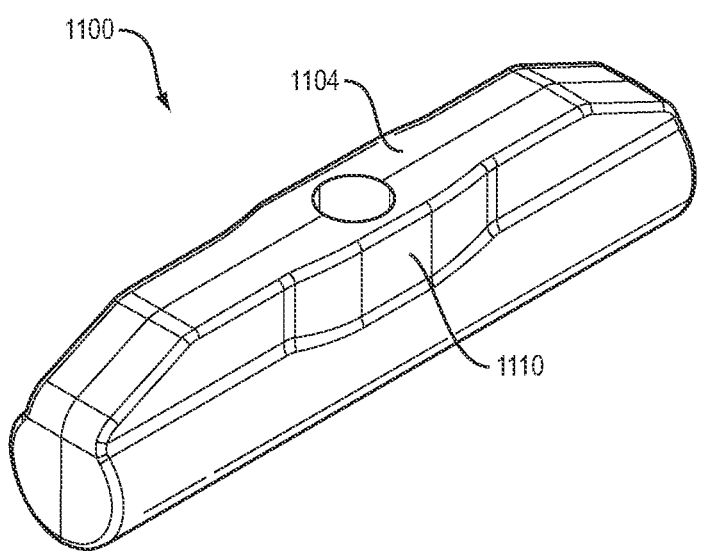

While the example of the proximal and distal anchors 622, 620 shown in FIGS. 6A-C comprises one projection 610 as a retaining feature, in other examples, the location, number and length of the retaining feature may vary. For example, in the anchor 900 shown in FIG. 9, the retaining feature comprises two projections 910a, 910b extending between the suture holes 908 and the beveled ends 916 on the sides of the rail 904. In the anchor 1000 shown in FIG. 10, the retaining feature comprises two projections 1010a, 10108 extending between the beveled ends 1016 on the sides of the rail 1004. FIG. 11 shows an example of a one-hole anchor 1100 having a single projection 1110. In the anchor 1100, the suture pathway would differ from that shown in FIG. 6C and the anchor 1100 may not contain a bottom suture recess. Nevertheless, each of the anchors 900, 1000, 1100 are symmetrical along both the length and width of the anchors 900, 1000, 1100 and the retention features extend along a majority of the sides of the rails 904, 1004, 1104. Notably, in each of the examples of the anchors 600, 900, 1000, 1100 described above, having the projections extend along a majority of the length of the sides of the rails contributes to the overall strength of the anchors.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. An anchor comprising:
   a generally cylindrical body having a top surface and a bottom surface, each of the top and bottom surfaces extending along a longitudinal axis between proximal and distal ends of the body; and
   a rail extending from the top surface of the body, the rail having a first end and a second end remote from the first end, the rail comprising a first projection extending between a first suture hole and the first end on a first side of the rail, and a second projection extending between a second suture hole and the second end on the first side of the rail, the first and second projections providing a retaining function when engaged with a mating surface of a delivery device.

2. The anchor of claim 1, further comprising a suture pathway including two internal parallel segments extending through the rail and the body.

3. The anchor of claim 2, wherein the two internal parallel segments each begin at a respective one of the first and second suture holes.

4. The anchor of claim 3, wherein the two internal parallel segments are connected by a third segment, each segment configured to slidably accommodate a suture.

5. The anchor of claim 4, wherein the third segment is formed in part by a recess in the bottom surface of the anchor.

6. The anchor of claim 1, wherein the first end and the second end of the rail are sloped toward the cylindrical body.

7. The anchor of claim 1, wherein the anchor is configured for slidable insertion into a bore of a needle having a slot such that the rail extends through the slot above the needle.

8. The anchor of claim 1, wherein the first side of the rail further comprises a first non-projecting region extending between the first suture hole and the second suture hole.

9. The anchor of claim 8, wherein the first side of the rail further comprises a first transition region between the first projection and the first non-projecting region, and a second transition region between the second projection and the first non-projecting region.

10. The anchor of claim 1, wherein a combined length of the first and second projections extends along a majority of a length of the first side of the rail.

11. The anchor of claim 1, wherein the rail further comprises a third projection extending between the first suture hole and the first end on a second side of the rail, and a fourth projection extending between the second suture hole and the second end on the second side of the rail.

12. The anchor of claim 11, wherein the second side of the rail comprises a second non-projecting region extending between the first suture hole and the second suture hole.

13. The anchor of claim 12, wherein the second side of the rail further comprises a third transition region between the third projection and the second non-projecting region, and a fourth transition region between the fourth projection and the second non-projecting region.

14. The anchor of claim 11, wherein a combined length of the third and fourth projections extends along a majority of a length of the second side of the rail.

15. The anchor of claim 11, wherein the anchor is symmetrical along a length and width of the anchor.

* * * * *